United States Patent [19]

Bruschi

[11] 4,089,747
[45] May 16, 1978

[54] COMPOSITIONS FOR THE DETECTION OF HYDROGEN PEROXIDE

[75] Inventor: Barbara Jungfleisch Bruschi, Fairport, N.Y.

[73] Assignee: Eastman Kodak Company, Rochester, N.Y.

[21] Appl. No.: 712,972

[22] Filed: Aug. 9, 1976

[51] Int. Cl.$^2$ ............................................. G01N 31/14
[52] U.S. Cl. ......................... 195/99; 195/103.5 UR; 195/103.5 R; 23/230 B; 252/408
[58] Field of Search .................. 195/103.5 R, 103.5 U, 195/99; 23/230 B; 252/408

[56] References Cited

U.S. PATENT DOCUMENTS

| 3,297,710 | 1/1967 | Silversmith | 252/408 |
| 3,630,847 | 12/1971 | Rey et al. | 195/103.5 R |

Primary Examiner—Alvin E. Tanenholtz
Attorney, Agent, or Firm—Arthur L. Girard

[57] ABSTRACT

There are disclosed buffered compositions for detecting either hydrogen peroxide or a substance having peroxidative activity by the catalytic oxidation of a dye-providing material by hydrogen peroxide in the presence of the material having peroxidative activity, which compositions comprise (A) hydrogen peroxide or substance having peroxidative activity, as appropriate, and
(B) as the dye-providing material, either
 (I) a mixture of
  (a) either a sulfonyl hydrazone of the formula

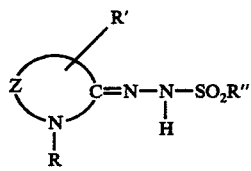

or a sulfonyl hydrazone precursor of the formula

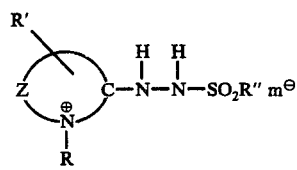

wherein
R = alkyl
R' = hydrogen, aryl, alkoxy, halogen or alkyl
R" = aryl or alkyl
Z = atoms necessary to complete a heterocyclic ring of 5–6 atoms in the ring nucleus
m$\ominus$ = an anion; and
 (b) a coupler or
 (II) a triarylimidazole of the formula

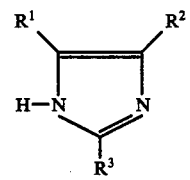

wherein $R^1$, $R^2$ and $R^3$ are each an organic group such that at least one of $R^1$, $R^2$ and $R^3$ is an ortho or para hydroxy substituted aryl group of up to 18 carbon atoms; the other two $R^1$, $R^2$ and $R^3$ being chosen such that the oxidation potential of the imidazole lies between −70 mV to +110 mV measured by cyclic voltometry against a standard calomel electrode using a carbon based electrode.

The method of utilizing such compositions and multilayer elements incorporating the same for the analysis of fluids suspected of containing hydrogen peroxide, substances having peroxidative activity or other analytes which produce hydrogen peroxide in their analysis are also described.

20 Claims, No Drawings

COMPOSITIONS FOR THE DETECTION OF HYDROGEN PEROXIDE

BACKGROUND OF THE INVENTION

1. Field of the Invention

This invention relates to novel compositions useful for detecting visually the presence of hydrogen peroxide and/or substances having peroxidative activity and particularly to compositions useful for detecting low levels of hydrogen peroxide.

The detection and quantitative determination of hydrogen peroxide and compounds yielding hydrogen peroxide are of importance in many areas, for example, in the detection of hydrogen peroxide produced in the enzymatic assay of substances such as glucose, cholesterol, uric acid, etc. by the activity of enzymes such as glucose oxidase, cholesterol oxidase, uricase, etc. in the presence of oxygen. The quantity of enzyme substrate present in a sample is determinable from the amount of hydrogen peroxide produced and detected.

Known compositions for detecting and/or quantifying hydrogen peroxide in such systems generally comprise a substance having perioxidative activity, e.g. peroxidase and peroxidase-like substances, and material which undergoes a detectable change (generally a color change) in the presence of hydrogen peroxide and the peroxidative substance. A complete list of the prior art which describes such compositions is too extensive for presentation here. However, a few representative patents which describe such materials are: U.S. Pat. Nos. 2,912,309, 2,981,606, 3,349,006, 3,092,465, 3,558,435, 3,595,755, 3,627,697, 3,627,698, 3,630,847, 3,654,179, 3,654,180 and 3,853,470. Examples of various color forming substrates of peroxidase and peroxidase-like substances which have been suggested in the prior art include, among others, the following substances with a coupler where necessary:

(1) Monoamines, such as aniline and its derivatives, ortho-toluidine, para-toluidine, etc.;

(2) Diamines, such as ortho-phenylenediamine, N,N'-dimethyl-para-phenylenediamine, N,N'-diethyl phenylenediamine, benzidine (which produces a blue or brown color), dianisidine (turns green or brown), etc.;

(3) Phenols, such as phenol per se (producing a yellow color), thymol, ortho-, meta- and para-cresols (producing a green-yellowing color, a pink color and a milky suspension, respectively), alpha-naphthol (producing a magenta color), betanaphthol (producing a white precipitate), etc.;

(4) Polyphenols, such as catechol, guaiacol (which forms an orange color), orcinol, pyrogallol (producing a reddish or yellow color), p,p-dihydroxydiphenyl and phloroglycinol;

(5) Aromatic acids, such as solicyclic, pyrocatechuic and gallic acids;

(6) Leuco dyes, such as leucomalachite green (to produce malachite green) and leucophenolphthalein (desirably employed in an alkaline medium);

(7) Colored dyes, such as 2,6-dichlorophenolindophenol;

(8) Various biological substances, such as epinephrine, the flavones, tyrosine, dihydroxyphenylalanine (producing an orange-reddish color) and tryptophane;

(9) Other substances, such as gum guaiac, guaiaconic acid, potassium, sodium, and other water soluble iodides; and bilirubin (producing a greenish color); and

(10) Such particular dyes as 2,2'-azine -di(3-ethylbenzothiazoline-(6)-sulfonic acid) and 3,3'-diaminobenzidine.

Although the above mentioned substances are in general useful as indicator systems for the detection of hydrogen peroxide, there are instances when the concentration of hydrogen peroxide to be analyzed is too low to produce sufficient detectable color from such indicators either due to the source of the hydrogen peroxide, the necessity for dilution, or the overall detection method. A specific example of such a concentration problem occurs in the detection of hydrogen peroxide produced from the low levels of uric acid present in blood serum (1–15 mg/dl). Where the environment of use permits compensation for this shortcoming of prior art compositions it is usually overcome by the measurement of relatively large volumes of the detectable product, e.g., by increasing the diameter of the cuvette in a solution assay for uric acid so as to additively increase the relative density of the color produced.

All analytical techniques do not, however, permit the use of such modifications to increase the effective density of indicator produced. In other applications the amount of indicator produced is small, due to either the initially very low concentration of analyte to be assayed using the hydrogen peroxide quantifying system or the necessity for high dilution levels to obtain proper dissolution or the like, that such manipulative approaches are not practical.

Such problems are particularly acute when the analyte determination is performed in a multilayer element of the type described in Belgian Pat. No. 801,742 issued Jan. 2, 1974 in the names of Przybylowicz and Millikan, and most acute when an analyte of low concentration, such as uric acid, is being assayed in such an element. In these cases, using the relatively thin indicator or reagent layers (on the order of less than a mil) that are desirable in such elements, the density of the color formed can be rather low. Increasing the thickness of the color-providing layer to provide greater density may be undesirable, as it can increase reaction times, create problems in layer preparation, etc. Consequently, other techniques for increasing the effective density of dye produced in the indicator reaction had to be found, if elements of this type were to be used reliably for the assay of low concentration blood serum components such as uric acid. The methods and compositions described herein are of course equally useful in the assay of materials and analytes, and specifically serum components, other than uric acid and in other media than multilayer elements and are particularly useful in assays requiring the detection of hydrogen peroxide where large dilutions of analyte solution are required for one reason or another.

SUMMARY OF THE INVENTION

Accordingly, it has now been discovered that low levels of hydrogen peroxide and/or substances having peroxidative activity can be readily detected using a buffered composition comprising, as appropriate, either hydrogen peroxide or a substance having peroxidative activity and an indicator comprising either (I) a mixture of (a) either a sulfonyl hydrazone of the formula

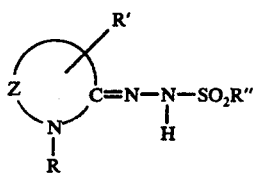

or a sulfonyl hydrazone precursor of the formula

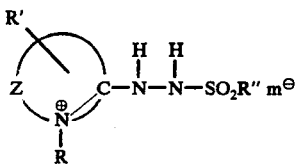

wherein
R = alkyl
R' = hydrogen, aryl, alkoxy, halogen or alkyl
R" = aryl or alkyl
Z = atoms necessary to complete a heterocyclic ring of 5-6 atoms in the ring nucleus
$m^{\ominus}$ = an anion; and
(b) a coupler or
(II) a triarylimidazole of the formula

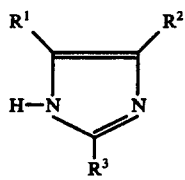

wherein $R^1$, $R^2$ and $R_3$ are each an organic group such that at least one of $R^1$, $R^2$ and $R^3$ is an ortho or para hydroxy substituted aryl group of up to 18 carbon atoms; the other two $R^1$, $R^2$ and $R^3$ being chosen such that the oxidation potential of the imidazole lies between about −70 mV to +100 mV measured by cyclic voltometry against a standard calomel electrode using a carbon based electrode.

Upon oxidation, the triarylimidazole yields a dye: a cyclohexadienylidine imidazole with an oxo group in conjugation with the imidazolyl group, e.g.

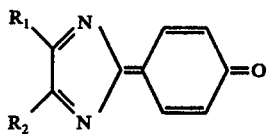

Thus, according to the present invention, there is also provided a process for the determination of hydrogen peroxide and of substances which react to produce hydrogen peroxide, as well as of peroxidase and other peroxidatively active substances. Such process comprises oxidizing a dye-providing material by hydrogen peroxide in the presence of peroxidase or other peroxidatively-active substance to form a colored dyestuff, the color intensity of which can be evaluated in the conventional manner to indicate the quantity of hydrogen peroxide or peroxidatively-active substance present in the specimen being analyzed. The colored dye-stuff fromed in such process is provided by an indicator (ie. dye-providing material) having a composition as described in I or II above.

The evaluation of the coloration can be carried out, for example, by optical measurement using a spectrophotometer or by comparison of the color intensity with standard color scales, comparison solutions or with color charts.

The determination of the presence of hydrogen peroxide by the process according to the present invention is particularly useful for coupled (i.e. combined sequential) and uncoupled (i.e. direct single step) enzyme reactions. This process is useful, for example, for the determination of glucose, galactose, amino acids, cholesterol and uric acid in coupled enzyme reactions and peroxides, hemoglobin, peroxidase or other peroxidatively-active substances in uncoupled enzyme reactions.

According to a further feature of the present invention, there are provided compositions for the determination of hydroperoxides or other analytes which can react to form hydrogen peroxide, which compositions comprise buffer, peroxidase or other peroxidatively-active substance, an indicator as in I or II above and the ingredients to achieve analyte reaction to form hydrogen peroxide.

According to yet another feature of the present invention, there is provided a diagnostic agent for the determination of hemoglobin and of other peroxidatively-active substances, which comprises hydrogen peroxide or a substance forming hydrogen peroxide and a dye-providing material as defined in I or II above.

It is further to be understood that the new diagnostic agents according to the present invention can be prepared in the form of solutions containing appropriate solvents and, if necessary, conventional adjuvants, such as surfactants. Alternatively, the new diagnostic agents can be prepared in the form of test papers by the impregnation of suitable absorbent materials, such as filter papers, with solutions of the components of the diagnostic reagents: Such solutions can also be used by making elements of the type described herein-after. In this connection, as in the case of the diagnostic solutions, it is frequently advantageous for the test papers to be prepared from solutions which contain conventional adjuvants, such as surfactants.

Furthermore, dry mixtures reconstitutable with water and comprising the dye-providing materials of formulas I and II above and either a substance forming hydrogen peroxide or a substance having peroxidative activity together with any necessary or desireable adjuvants, such as surfactants, are also within the contemplated scope of the instant invention.

The buffered compositions of the present invention produce dyes which, as will be demonstrated by the examples and description which follow, have very high extinction coefficients and hence produce relatively high densities for relatively small concentrations of dye. Thus a means is provided for detecting relatively very low concentrations of hydrogen peroxide, peroxidative substances or analyte which produces hydrogen peroxide in analysis. This is particularly advantageous when such analyses are performed using a multilayer element as described in the above-referenced Belgian patent because there is no need for an increase in the thickness of the reagent medium or other manipulative modifications.

Finally, mention should be made of the fact that the process according to the present invention can, in addition, be used for the determination of the dye-providing materials described in I and II above utilizing for such determination a composition comprising both hydrogen peroxide or a H₂O₂ forming materials and a peroxidatively-active substance. This assay may be useful for control purposes in the preparation of diagnostic materials of this type.

Description of the Preferred Embodiments

Compositions for the detection of hydrogen peroxide are well known in the art, particularly as indicator compositions in the enzymatic detection of glucose, uric acid, cholesterol and other enzyme substrates. Such hydrogen peroxide-detecting compositions generally comprise a substance having peroxidative activity, preferably peroxidase and dye-providing material which undergoes a color formation or change in the presence of hydrogen peroxide and the peroxidative substance. The dye-providing material may represent a material, e.g. a leuco dye, which undergoes a color change directly; or it may represent a material which undergoes no substantial color change upon oxidation in the presence of H₂O₂ and peroxidase, but which in the oxidized form reacts with a coupler which is part of the indicator composition to give detectable products preferably on a stoichiometric basis. Color forming compositions which produce color by virtue of color coupling reaction and those which undergo direct color formation are of the type described herein.

As will become apparent from the results shown in Example 1 below, not all of the dye-providing materials described by the aforementioned structural formulas will produce color in the presence of hydrogen peroxide and substance having peroxidative activity and any buffer. Consequently, it is important to determine the operability of indicator compositions of the type described herein with a screening test of the kind described in Example 1. This screening is accomplished by mixing, in a test tube, a small amount of the dye-providing material under evalation (in a water miscible solvent such as methanol if water solubility is a problem) together with the peroxidatively-active substance and a buffer of choice. A small amount of hydrogen peroxide is then added and the color formation observed. If no color appears, this negative result may be due to the redox potential of the dye-providing material in the particular buffer system selected or simply that the oxidation potential of the dye-providing material is too high for oxidation to occur in the presence of the particular peroxidatively-active material and hydrogen peroxide. Thus, using routine laboratory procedures together with various dye-providing materials, buffers and peroxidatively active materials, one can select high extinction coefficient dye-producing compositions suited to the particular coupled or uncoupled assay under consideration.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms and may be produced by fermentation. Certain synthetic peroxidases, such as those disclosed by Theorell and Maehly in Acta Chem. Scand, Vol. 4, pages 422–434 (1950), are also satisfactory for use in H₂O₂ detection systems. Less satisfactory are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides.

Other substances which are not enzymes but which demonstrate peroxidative activity are: iron sulfocyanate, iron tannate, ferrous ferrocyanide, chromic salts (such as potassium chromic sulfate) absorbed in silica gel, etc.

Dye-providing materials according to the present invention comprise either:

(I) a mixture of
(a) either a sulfonyl hydrazone of the formula

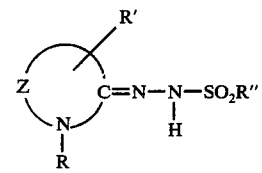

or a sulfonyl hydrazone precursor of the formula

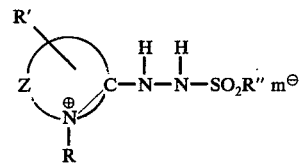

wherein
R = alkyl
R' = hydrogen, aryl, alkoxy, halogen or alkyl
R" = aryl or alkyl
Z = atoms necessary to complete a heterocyclic ring of 5–6 atoms in the ring nucleus
$m^\ominus$ = an anion; and
(b) a coupler or
(II) a triarylimidazole of the formula

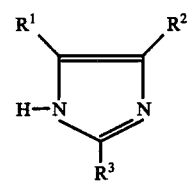

wherein $R^1$, $R_2$ and $R^3$ are each an organic group such that at least one of $R^1$, $R_2$ and $R_3$ is an ortho or para hydroxy substituted aryl group of up to 18 carbon atoms; the other two $R^1$, $R^2$ and $R^3$ being chosen such that the oxidation potential of the imidazole lies between about −70 mV to +110 mV measured by cyclic voltometry against a standard calomel electrode using a carbon based electrode.

As used herein, the term aryl is meant is include aromatic hydrocarbon groups, e.g., phenyl naphthyl, etc., including substituted aromatic groups. Reference herein to the number of carbon atoms in an aryl group refers to the total number of carbon atoms in the aromatic group including substituents. Alkyl refers herein preferably to alkyl groups, including substituted alkyl groups, of from 1 to about 20 carbon atoms (most preferably 1–10 carbon atoms) in the aliphatic chain used to established the nomenclature for that group. Useful substituents on the R, R' and R" groups attached to the compounds or I include electron withdrawing groups such as halogen, hydroxyl, cyano, nitro, etc. Useful salt-forming anions, m⊖, of compounds of I include p-toulene sulfonate, alkylsulfate, sulfate, chloride, bromide, iodide, etc.

The preparation and reactivity of the sulfonyl hydrazones of I above are described in detail in the following publication and related earlier publications referenced therein: Agnew. Chem. Internat. Edit., 7, 355–344 (1968). As described in this publication, compounds of formula I are prepared by one of the following methods depending upon the availability of starting material:

(a) Reactive quaternary salts such as III, V or VII are allowed to react with sulfonyl hydrazones as follows:

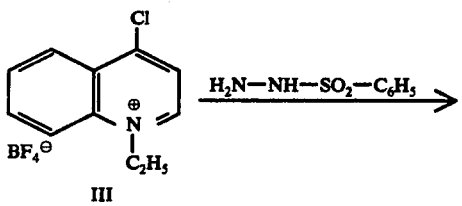

III

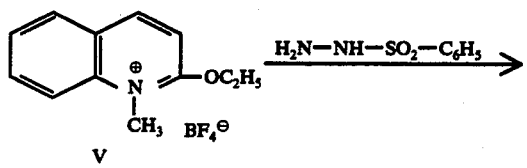

V

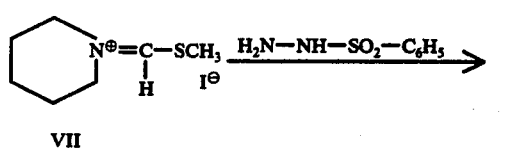

VII

VIII

Halogens, SR and OR wherein R is alkyl have been found to be good leaving groups from these reactive quaternary salts.

(b) If the hydrazone is available, it may be sulfonated with sulfonyl chlorides as follows:

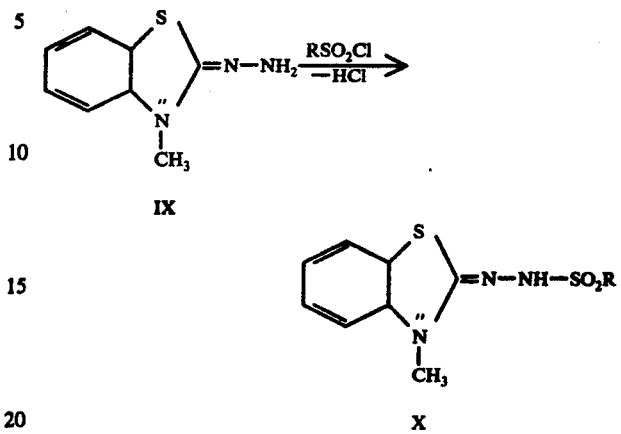

IX

X

Where R is hydrogen or an alkyl group.

(c) 2-Thiazolonesulfonyl hydrazones are most easily synthesized from α-halogeno ketones and benzenesulfonyl thiosemicarbazides as follows:

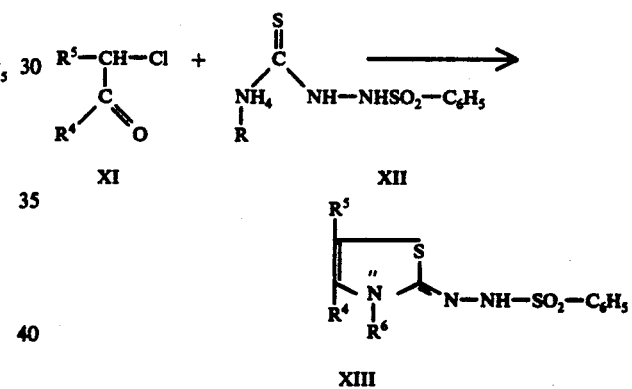

XI    XII

XIII wherein
$R^4$ = H, alkyl or aryl
$R^5$ = H or alkyl
$R^6$ = alkyl or aryl.

According to a preferred embodiment the sulfonyl hydrazone precursor comprises a salt of the formula

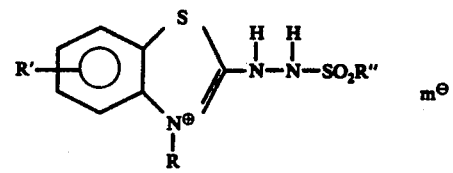

wherein R, R', R" and M⊖ are as defined hereinabove. In use such compounds are first deprotonated to the hydrazone which then couples with the coupler of that mixture.

Specifically preferred from among these salts are those where m = p-toluenensulfonic acid.

The following are structural formulae of preferred such hydrazone precursor compounds:

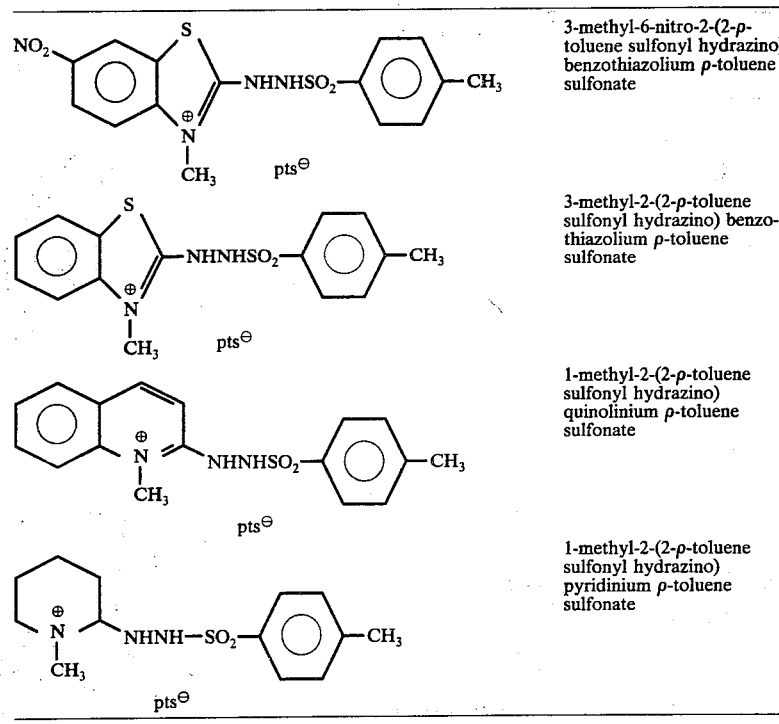

| Structure | Name |
|---|---|
| 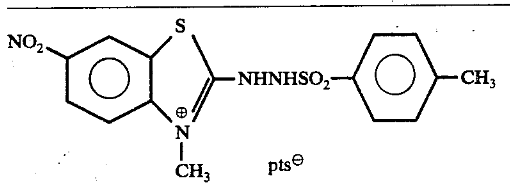 | 3-methyl-6-nitro-2-(2-p-toluene sulfonyl hydrazino) benzothiazolium p-toluene sulfonate |
| 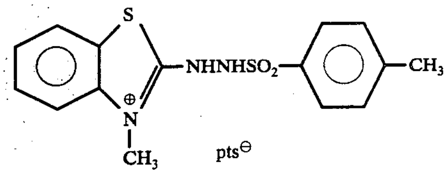 | 3-methyl-2-(2-p-toluene sulfonyl hydrazino) benzothiazolium p-toluene sulfonate |
| 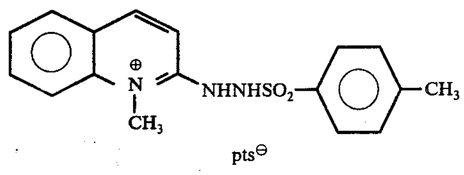 | 1-methyl-2-(2-p-toluene sulfonyl hydrazino) quinolinium p-toluene sulfonate |
| 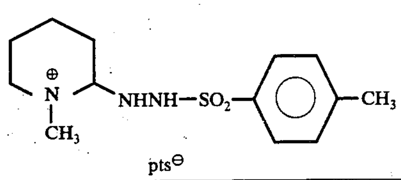 | 1-methyl-2-(2-p-toluene sulfonyl hydrazino) pyridinium p-toluene sulfonate |

As should be clear to those skilled in the art and as referred to above, it is, of course, necessary to appropriately match the dye-providing material and coupler since not all such dye-providing materials will combine with all couplers in all buffer systems to provide useful results. The screening test described above is useful in this regard. Useful couplers include phenol, naphthol, aromatic amine or reactive methylene couplers. Specific such couplers include: 1-napthol, 2-naphtol, 5-dimethylamino-1-naphthalenesulfonic acid, 2,6-dimethylphenol, phenol, diphenylamine, 4-chloro-2-nitrophenol, -hydroxyphenyl acetic acid, 4-chloro-3-methylphenol, 2,4-dichloro-1-naphthol, and 4-chloro-2,6-dinitrophenol.

Preferred triarylimidazole dye precursors are those of the formula

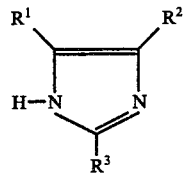

wherein $R^1$, $R^2$, $R^3$ are each an organic group such that at least one of $R^1$, $R^2$, $R^3$ is an ortho or para hydroxy substituted aryl group of up to 18 carbon atoms and at least one other of $R^1$, $R^2$, $R^3$ has an ortho or para electron donating substituent group such as an alkyloxy group (—OR) wherein R = alkyl of from 1 to about 8 carbon atoms; or dialkylamino $(R)_2N$—where R is alkyl group of 1 to about 8 carbon atoms.

The preparation and reactivity of useful triarylimidazole dye precursors are described in U.S. Pat. No. 3,297,710 issued Jan. 10, 1967.

Useful substituents on the $R^1$, $R^2$ and $R^3$ groups of the imidazole materials include halogen, hydroxyl, cyano, haloalkyl, cyanoalkyl, hydroxyalkyl, aminoalkyl, aryl, aroxyl, aralkoxy, alkylthio, arylthio, aralkylthio, alkanoyl, aroyl, alkyl, sulfonyl, arylsulfonyl, dialkylamino, trialkyl ammonium, alkoxy carbonyl, aryloxycarbonyl, and dialkylaminocarbonyl. Preferably, alkyl stands for the $C_1$-$C_5$ radicals, and aryl stands for aromatic hydrocarbon radicals, e.g., phenyl. Each of these substituent groups is electronically compatible with the heretofore described chromophoric units of this invention.

The following is a list of triarylimidazole dye-providing materials useful in the compositions described herein:

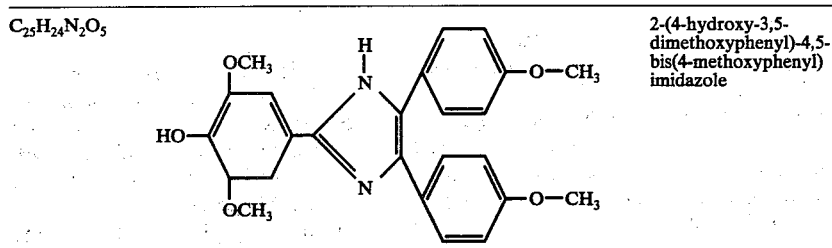

$C_{25}H_{24}N_2O_5$ — 2-(4-hydroxy-3,5-dimethoxyphenyl)-4,5-bis(4-methoxyphenyl) imidazole -continued

| | | |
|---|---|---|
| $C_{21}H_{14}Br_2N_2O$ | 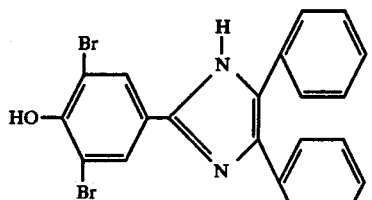 | 2-(3,5-dibromo-4-hydroxy-phenyl)-4,5-diphenylimidazole |
| $C_{24}H_{21}BrN_2O_4$ | 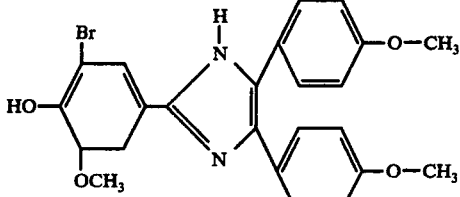 | 2-(3-bromo-5-methoxy-4-hydroxyphenyl)-4,5-bis(4-methoxyphenyl)imidazole |
| $C_{25}H_{26}N_4O$ | 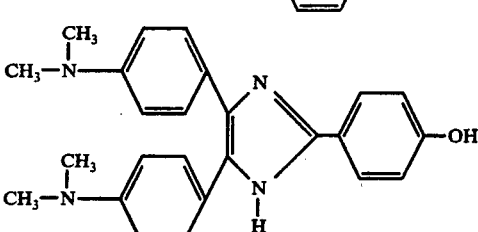 | 4,5-bis(4-dimethylamino-phenyl)-2-(4-hydroxyphenyl)imidazole |
| | 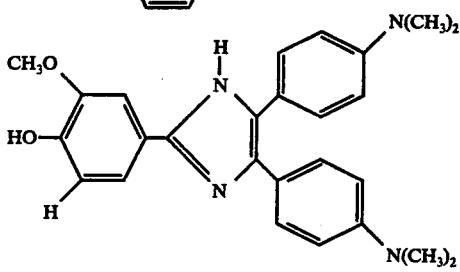 | 4,5-bis(4-dimethylamino-phenyl)-2-(4-hydroxy-3-methoxyphenyl)imidazole |
| | 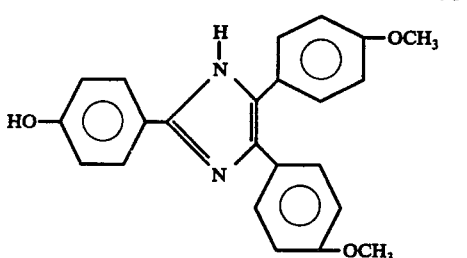 | 2-(4-hydroxyphenyl)-4,5-bis(4-methoxyphenyl)imidazole |
| | 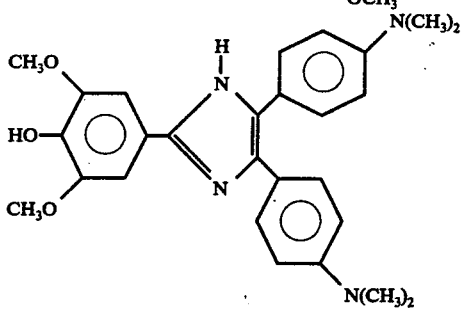 | 4,5-bis(4-dimethylamino-phenyl)-2-(4-hydroxy)-3,5-dimethoxyphenyl)imidazole |

Other representative imidazoles which fall within the scope of the heretofore defined structure are given in aforementioned U.S. Pat. No. 3,297,710.

Substantially any buffer is a suitable candidate for use in the composition described herein. Useful buffers will, of course, establish the pH of the reaction medium at a level which is conducive to the occurrence of the chromogenic reaction while not inhibiting the reaction. The screening test described hereinabove and demonstrated in Example 1 below is useful in determining the utility of particular buffers in the compositions described herein. We have found that useful buffers include carbonate buffers such as sodium and potassium carbonate, borate buffers such as sodium and potassium borate, citrate, phosphate and glutarate buffers and the tris materials such as tris(hydroxymethyl)aminomethane. Some of these materials buffer the reagent composition to a range of between about 5.0 and 10.0 which is a useful pH range for detecting, for example, blood serum components using the particular indicator described herein in coupled enzymatic reaction sequences such as those useful in the assay of glucose using glucose oxidase to produce hydrogen peroxide. When used to detect uric acid using uricase, it is preferred to buffer the composition to a pH between about 8 and about 9.

The compositions described herein may be incorporated into bibulous or absorbent analytical elements of the type well known in the art.

The novel compositions of the present invention can be incorporated into fibrous filter paper type testing materials or more sophisticated and highly preferred multilayered analytical elements of the type described in Belgian Pat. No. 801,742 of E. P. Przybylowicz and A. G. Millikan.

Elements of this type comprise:
(1) a spreading layer;
(2) a reagent layer which is in fluid contact with the spreading layer under conditions of use; and
(3) optionally, a support.

Preferred elements of this type employ a non-fibrous spreading layer.

Multilayer analytical elements of this type are adapted to carrying out individual analyses or multiple analyses with the aid of continuous analyzers. These elements may be utilized in the form of a continuous strip, a sheet, or as discrete chips.

Reference herein to fluid contact between a spreading layer and a reagent layer in an integral analytical element identifies the ability of a fluid, whether liquid or gaseous, to pass in such element under conditions of use between superposed regions of the spreading layer and the reagent layer. Stated in another manner, fluid contact refers to the ability of components of a fluid to pass between the layers in fluid contact. Although such layers in fluid contact can be contiguous, they may also be separated by intervening layers as described in detail hereinafter. However, layers in the element that physically intervene a spreading layer and reagent layer in mutual fluid contact will not prevent the passage of fluid between the fluid contacting spreading and reagent layers. Fluid contact between layers can be achieved by preparing elements having layers that are contiguous or effectively so for purposes of fluid passage. Alternatively, it may be appropriate to prepare elements that have layers initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has intially non-contiguous layers, it may be necessary to apply compressive force or otherwise to bring layers of the element into fluid contact at the time of its use to provide an analytical result.

The Spreading Layer: As used herein, the term spreading layer refers to a layer, isotropically porous or otherwise, that can accept a liquid sample, whether applied directly to the spreading layer or provided to it from a layer or layers in fluid contact with the spreading layer, and within the layer distribute (i.e., meter) the solvent or dispersion medium of the sample and at least one dissolved or dispersed component such that a uniform concentration of such component is provided at the surface of the spreading layer facing the reagent layer(s) of the element. It should be understood that the uniformity of such concentration is a uniformity as measured by techniques like those described hereinafter. As such, the uniform concentration can also be termed a uniform apparent concentration. (The spreading layer is synonymously referred to herein as the metering layer.) In the context of this invention, the spread component will include analyte. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The spreading layer can be an isotropically porous layer. Reference herein to isotropic porosity identifies the fact of substantial porosity in all directions within the spreading layer. It will be understood that the degree of such porosity may be variable, if necessary or desirable, for example, regarding pore size, percentage of void volume or otherwise. It shall be understood that the term isotropic porosity (or isotropically porous) as used herein should not be confused with the terms isoporous or ionotropic often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See for example, *Membrane Science and Technology*, James Flinn Ed, Plenum Press, New York (1970).

As will be appreciated, the extent of spreading is dependent in part on the volume of liquid to be spread. However, it should be emphasized that the uniform apparent concentration obtained with spreading is substantially independent of liquid sample volume and will occur irrespective of the extent of spreading. As a result, elements of this invention generally do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., one square centimeter), there is no need to remove excess moisture from the element after application of a liquid sample, further, because spreading occurs in the spreading layer and the spread component is provided to the fluid contacting reagent layer without apparent substantial lateral hydrostatic pressure, there is not the "ringing" problem often seen with prior analytical elements when soluble reagents were used.

The spreading layer need only produce a uniform concentration of spread component per unit area at its surface facing a reagent layer with which the spreading layer is in fluid contact in use, and it is convenient to determine whether a particular layer can be suitable for spreading purposes by means of the following simple test.

This test is intended only as an example and the selection of materials or test parameters does not indicate, expressly or by implication, that other materials or parameters would not be suitable for similar purposes.

In conducting such a test one can apply to a transparent photographic film support material, such as subbed poly(ethylene terephthalate), a transparent gelatin layer at a gelatin coverage of about 200 mg/dm$^2$. The gelatin may vary in hardness, but for testing purposes a layer of gelatin hardened to swell the layer thickness by about 300% when immersed for 5 minutes in 22° C water is suitable. When dry, the gelatin layer will have a thickness of about 30 microns. Over the gelatin layer can be applied, such as by coating from solution or dispersion, the layer to be evaluated for spreading purposes. Spreading layers can be designed to have widely varying dry thicknesses, and a thickness of from about 100 to about 200 microns is convenient for test purposes. After drying the layers, a sample of test solution or dispersion can be applied to the surface of the spreading layer under evaluation, preferably in a small quantity so that not all portions of the layer are wetted by the applied sample, but desirably sufficient to create a wetted region such as one having a circular area of about 8–10 millimeters in diameter. The selection of a test solution or dispersion is a matter of choice and will depend in part on the type of sample or analyte to which the layer will be exposed under conditions of actual usage. For low molecular weight materials, aqueous dye solutions can be used and a .0005 weight percent solution of Solatine Pink ® is acceptable. For higher molecular weight materials such as proteins, an aqueous dispersion of bovine albumin dyed with Solatine Pink ® can be used. After applying the liquid sample to the layer under evaluation and allowing the liquid sample to disappear from the surface and be taken up into the layer, the test element can be turned over and the bottom surface of the proposed spreading layer can be viewed through the transparent support material and gelatin layer. If, prior to substantial evaporation of solvent or dispersion medium, the test element exhibits a well-defined colored spot of a substantially uniform color density when scanned by a densitometer having an aperture of about 5 microns by 100 microns, then spreading and the achievement of a uniform apparent concentration at the bottom surface of the test layer and/or in the gelatin layer has taken place. By substantially uniform density is meant a density across the spot, with the exception of its periphery, having maximum and minimum values not more than about ± 10% from the mean density. Due to dge effects, non-characteristic density gradients may arise at the spot periphery but need have no effect on the significance of an analytical result. Peripheral area can vary between spots, but it will usually not be more than about 20% of the entire spot and may be less.

Isotropically porous layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such microcrystalline materials are described in an article entitled "Colloidal Macromolecular Phenomena, Part II, Novel Microcrystals of Polymers" by O. A. Battista et al published in the *Journal of Applied Polymer Science*, Vol. II, pages 481–498 (1967). Microcrystalline cellulose, which is commercially available from FMC Corporation under the name Avicel ®, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non adherent particles can be coated with a thin adherent layer, such as a solution of hydrophilic colloid like gelatin or polyvinyl alcohol, and brought into mutual contact in a layer. When the colloid (i.e., binder) coating dries, the layer integrity is maintained and open spaces remain between its component particles.

Other techniques useful in preparing isotropically porous polymer compositions include those relating to the use of gas or other swellable constituents to create pores, as described in U.S. Pat. Nos. 2,960,728 and 2,946,095; to the use of precipitation techniques, as described in U.S. Pat. No. 3,555,129; or to the use within the polymer phase of a dissolvable solid that is dissolved to provide pores, as discussed in U.S. Pat. No. 3,816,575.

"Blushed" or precipitated polymer layers are particularly desirable and can be formed on a substrate by dissolving a polymer in a mixture of two liquids, one of which is a lower boiling, good solvent for the polymer and the other of which is of a higher boiling point and is a non-solvent or at least a poor solvent for the polymer. Such a polymer solution is then coated on the substrate, and dried under controlled conditions. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous "blush" polymer spreading layers for use in this invention, typical examples being polycarbonates, polyamides, polyurethanes and cellulose esters such as cellulose acetate. Various microporous filters comprised of blushed polymeric compositions are also useful, for example, various membrane filters or Millipore Corporation, which have been described in patents such as U.S. Pat. 2,783,894 and U.S. Pat. No. 2,772,322.

A wide range of materials are useful as the spreading layer. Usually, however, materials that are resistant to, i.e., substantially non-swellable upon contact with, the liquid under analysis are desired. Swelling of about 10–40% of the layer's dry thickness may be normal.

In addition to the foregoing, it is highly desirable that the spreading layer be non-fibrous. The term "non-fibrous" is used herein with respect to layers and/or materials to indicate that such layers or materials are free, or substantially free, from fibrous materials, that is, they do not include fibrous components to a degree that would interfere with sample spreading as discussed herein or with detection of the analytical result by radiometric means.

The Reagent Layer(s): Reagent layers in the elements of this invention are desirably permeable, preferably uniformly permeable, and optionally porous if appropriate, to components spreadable within the metering or spreading layer. As used herein, the term permeable includes permeability arising from porosity, ability to swell or any other characteristic. Such layers generally include a matrix in which is distributed, i.e., dissolved or dispersed, materials that are interactive with analyte. Exemplary interactive materials are discussed under "Reagents."

The distribution of interactive materials (i.e., reagents) can be obtained by dissolving or dispersing them in the matrix material. Although uniform distributions of reagents are often preferred, they may not be necessary if the interactive material is, for example, an enzyme such as uricase.

Desirably, reagent layers are uniformly permeable to the spread components. Uniform permeability of a layer refers to permeability such that, when a homogeneous fluid is provided uniformly to a surface of the layer, measurements of the concentration of such fluid within the layer, made with identical equipment and under identical conditions but through different regions of a surface of the layer, will yield (i.e., be capable of yielding) substantially equal results. By virtue of uniform permeability, undesirable concentration gradients within, for example, a reagent layer as described herein, are avoided.

The elements hereof may also include registration layers, i.e. layers which underlie spreading and reagent layers, contain no interactive materials and serve only to receive dyes produced in the overlying layers. Such layers generally comprise a matrix permeable to the dye and as desired other adjuvants such as mordants, surfactants etc. which enhance layers and their arrangement in analytical elements are described in more detail in Belgian Patent No. 831,660 published Jan. 23, 1976 in the name of P. Clement and entitled "Integral Element for Analysis of Liquids."

The choice of a matrix material for the reagent or registration layers described herein is, of course, variable and dependent on the intended method of use of the element as well as the particular interactive materials which are incorporated therein as described hereinafter. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use parameters for any particular element. To enhance permeability of the reagent layer, if not porous, it is often useful to use a matrix material that is moderately swellable in the solvent or dispersion medium of liquid under analysis.

In addition to its permeability, the reagent layer is desirably substantially free from any characteristic that might appear as or contribute to mottle or other noise in the detection of an analytical result produced in the integral element. For example, variations in color or in texture within the reagent layer, as may occur in fibrous materials such as papers are used as a permeable medium, may be disadvantageous due to non-uniform reflectance or transmittance of detecting energy, e.g., when the detectable change has occurred in and is detected in the reagent layer. Also, although fibrous materials like filter and other papers are highly permeable overall, they typically exhibit widely ranging degrees of permeability between regions of the paper, for example, based on structural variations such as fiber dimensions and spacing. As a result, such materials are not considered uniformly permeable and, as such, are not preferred in reagent layers and other layers of the present invention which preferably comprise non-fibrous material.

Supports: The integral analytical elements can be self-supporting or the spreading layer, reagent layer and any other associated layers can be coated on a support. Useful support materials, when such are used, include paper and polyolefin coated paper, as well as a variety of polymeric materials such as cellulose acetate, poly(ethylene terephthalate), polycarbonates and polyvinyl compounds such as polystyrenes, etc. The support can be opaque or it can transmit light or other energy depending, of course, on the mode of detection used. A support of choice in any case will be compatible with the intended mode of result detection. Preferred supports include transparent support materials capable of transmitting electromagnetic radiation of a wavelength within the region between about 200 nm and about 900 nm. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer is interposed in the element between the support and the spreading layer. Specifically preferred transmission ranges for elements of the present invention will be apparent from the discussion of the various preferred indicator compositions discussed above. When used, supports having thicknesses of between about 1 and about 10 mils have been found satisfactory, although the thickness can vary broadly depending on such factors, for example, as the intensity of the detecting radiation and the sensitivity of the detecting apparatus.

Other Layers: The analytical element of the present invention is preferably adapted for use in an analytical system employing reflection techniques of spectrophotometric analysis, and consequently generally includes a layer which functions as a reflecting layer and thereby provides a suitable background for spectrophotometric measurement of colorimetric or other indicator reactions through the support side of the element. The reflecting layer will permit the passage of analyte to the reagent or registration layer and should provide an effective background for reflection spectrophotometry. A white background is generally preferred for this purpose. In view of its function as a background for indicator formed in the reagent or registration layer, any reflective layer will normally intervene the spreading and reagent or registration layers. Such a layer may, however, intervene a reagent and registration layer where such structure is appropriate. Reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Filtering layers may also be present in the element. The composition and preparation of such layers are well known in the art and, when present, they serve to remove from the sample components which could interfere with the indicating reaction or otherwise hinder quantification. Thus, in the use of the multilayer analytical element for analysis of uric acid in whole blood, a separate filtering layer could serve to remove red blood cells while transmitting the serum to the layer below. In the analysis of blood serum or other fluids, the filtering layer may serve to remove unwanted components which could hinder or confuse the primary indicating reaction. Alternatively, the aforementioned blush polymer layers may also serve as filtering layers. If the element is to be used for analysis of whole blood, it is desirable that any filtering layer have a pore size of 0.5 to 5 microns.

In order to increase adhesion of the reagent layer to the superimposed spreading, filtering, and reflective layer(s) it has been found advantageous in some cases to apply a permeable separating or interlayer which serves as a subbing layer to improve adhesion between such layers. So long as the interlayer is sufficiently permeable to permit the analyte to reach the reagent layer, does not inhibit any reagents in adjacent layers, and provides the adhesion improvement desired, it may be formed of almost any material. Such materials are well known to those skilled in the art.

Among the interlayer materials which have provided particularly advantageous results are polymeric film forming materials such as poly(n-vinyl-2-pyrrolidone), poly(n-isopropylacrylamide), copoly(vinyl acetate/vinyl neodecanoate) (20 wt. percent vinyl acetate), and copoly(vinyl neodecanoate/n-vinyl-2-pyrrolidone) (10 and 30 wt. percent vinyl neodecanoate).

Since it is critical that the permeability of the interlayer be maintained, these layers are necessarily very thin and may generally range in thickness from monolayers of materials on up to layers on the order of 1 mil. When polymeric interlayers of the materials mentioned above are used, these are generally applied at levels ranging from about 90 mg/m$^2$ to about 1000 mg/m$^2$ depending on such properties as the density of the polymer, the permeability of the ultimate subbing layer, etc.

Surface treatments which improve adhesion between layers, for example, electron bombardment, etc. may also be desirable.

Element Preparation: In preparing integral analytical elements of this invention, the layers can be preformed as separate layers and thereafter laminated or maintained as separate layers until brought into fluid contact when the element is used. Layers prepared as separate members are typically coated from solution or dispersion on a surface from which the layer can be physically stripped when dried. However, a convenient procedure which can avoid the necessity for multiple stripping and lamination steps when contiguous layers are desired is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. Interlayer adhesion problems can be overcome without harmful effect by means of surface treatments including extremely thin application(s) of subbing materials such as are used in photographic films.

Certain of the reagent materials may be incorporated into the spreading layer. Specifically the enzyme uricase can be incorporated into this layer to obtain hydrogen peroxide production before the sample reaches the reagent layer containing the materials which act upon the $H_2O_2$ to produce a detectable change.

According to one embodiment of the present invention, wherein the spreading layer performs the functions of filtering and spreading, the layer is advantageously prepared by simultaneously coating two strata of a binder such as cellulose acetate dissolved in a mixed organic solvent to provide "blush" polymer layers as described herein. Such a technique simplifies the manufacturing operation by reducing the multiple coating of multiple layers to a single multiple coating operation while providing a highly useful spreading and/or filtering layer. Optionally, if desired, either or both of the discrete layers may contain dispersed therein a reflective pigment such as $TiO_2$.

Equipment and techniques suitable for simultaneous coating of various individual layers within either the spreading layer or the reagent layer are described in U.S. Pat. No. 2,932,855 issued Apr. 19, 1960.

The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers having a thickness of from about 50 microns to about 300 microns have been particularly useful, although wider variations in thickness are acceptable and may be desirable for particular elements.

When preparing an isotropically porous spreading layer, it is useful to have a void volume comprising at least about 25% of the total layer volume, and void volume of from 50-95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous "blush" polymers are used in the spreading layer. The void volume of any such layer can be calculated with reasonable accuracy by a variety of techniques such as the statistical method described in Chalkley, *Journal of the National Cancer Institute*, 4, 47 (1943) and by direct weighing and determining the ratio of actual weight of the layer to the weight of solid material equal in volume to that of the layer comparably composed of constituents from the layer.

For reagent layers, a coating solution or dispersion including the matrix and incorporated interactive materials can be prepared, coated as discussed herein, and dried to form a dimensionally stable layer. The thickness of any reagent layer and its degree of permeability are widely variable and depend on actual usage. Dry thicknesses of from about 10 microns to about 100 microns have been useful.

Furthermore, the element may incorporate several discrete reagent layers, each of which performs a specific operation in the analytical procedure. In one embodiment, the reagent system for the determination of uric acid may be coated in two discrete layers. The uppermost of these layers can contain the reagents necessary for hydrogen peroxide generation from uric acid and the second could contain the color or other indicator system.

In an analytical element for the assay of uric acid the enzyme uricase is incorporated in either the spreading or reagent layer at coverages of about 50 to 500 $U/m^2$ and preferably at coverages of about 100 to 300 $U/m^2$. Peroxidase may be employed in such an element at coverages of about 1,000 to 10,000 $U/m^2$ and preferably at coverages of about 2,000 to 8,000 $U/m^2$.

In a preferred embodiment, the layers described herein are formed by coating from solutions or dispersions, for example, as described in the aforementioned Przybylowicz and Millikan application. For coating purposes, it is often necessary to include coating aids which impart appropriate coating properties to the layers.

Whatever coating aids are used for this purpose, for those described below, it is important that they do not inhibit the activity of uricase or any of the other reagents present in any of the various reagent layers. Particularly useful coating aids for this purpose include nonionic surfactants such as the octyl phenoxy polyethoxy ethanols commercially available from Rohm and Haas Co. under the Triton tradename (X-100, 102, 165, 305, and 405 being particularly useful), (p-nonylphenoxy) glycerol commercially available from Olin Mathieson Corp. under the tradename Surfactant 10G, and the carbowax polyethylene glycols 600, 1540, 4000, 6000 and 20M available from Union Carbide, the oleyl either of Carbowax 1540 being particularly useful. Other useful coating aids are glycerine and Alkanol XC (triisopropyl naphthalene sulfonate, sodium salt) commercially available from Dupont.

Surfactant levels on the order of from about 0.5 to about 4.0 $g/m^2$ in the reagent layer and from about 1.0 to about 5.0 $g/m^2$ in the spreading layer have been generally found to produce no or minimal inhibitory effects while providing improved coating and sample spreading characteristics.

Hardeners can be used in layer preparation to insure proper and rapid set of the vehicle, to prevent damage on handling and to inhibit undesirable intermixing of adjacent layers. Their use is well known in the art and well documented and hence no further discussion is presented herein. Whatever organic or inorganic hardeners are used for this purpose, it is important that they do not adversely affect any of the other reagents present in the layers to any great degree. Hardeners which have been found particularly useful for this purpose include glutaraldehyde and bis(vinylsulfonylmethyl)-ether.

Use of the Element: Thus, in use, as demonstrated by the uric acid determination examples which follow, a drop size sample on the order of from about 5 to about 50 μl is applied to the spreading or other outermost layer using known drop application techniques. In passage through the spreading layer the sample drop is spread so that a metered amount thereof is delivered to the underlying reagent layer wherein the degradation of the uric acid and production of hydrogen peroxide occur.

Alternatively, depending on the embodiment used, the production of the hydrogen peroxide may occur in the spreading layer or an upper reagent layer, and a metered amount of the hydrogen peroxide delivered to the underlying reagent layer. In either case, the hydrogen peroxide is quantitated in a reagent layer using the indicator system of choice and known techniques, and the concentration of total uric acid present in the applied sample determined.

The following examples are included to illustrate further the present invention.

EXAMPLE 1

In order to illustrate the use of certain indicators for hydrogen peroxide detection and of composition as described herein to detect small amounts of $H_2O_2$ in solution, a number of compounds were screened by preparing solutions buffered from pH 8.5 to 9.8 with either carbonate, borate or tris buffers. Such solutions were prepared by dissolving a small amount of the candidate indicator composition in methyl alcohol in a test tube, adding aqueous buffer solution and a small amount of peroxidase. A small amount of peroxide was then added and the resultant color noted. The couplers used in combination with the hydrazone compounds were as follows:

1. 2-naphthol
2. 5-dimethylamino-1-naphthalenesulfonic acid
3. 2,6-dimethylphenol
4. phenol
5. diphenylamine The results of this testing are shown in Table I.

As used in Table I the term positive indicates that a detectable quantity of dye was produced and the term negative indicates that no detectable amount of dye was produced.

Table I

| I. Dye-Providing Material Structure | Coupler | Reaction-Color | Buffer System |
|---|---|---|---|
| [structure with $NO_2$, S, N⁺-CH₃, pts⁻, -NHNHSO₂-, CH₃] | (1)<br>(2)<br>(3)<br>(4)<br>(5) | neg.<br>neg.<br>pos.-dk. orange<br>pos.-red-brown<br>neg. | all 3<br>all 3 |
| [structure with S, N⁺-CH₃, pts⁻, -NHNHSO₂-, CH₃] | (1)<br>(2)<br>(3)<br>(4)<br>(5) | neg.<br>neg.<br>pos.-red<br>pos.-orange-red<br>neg. | tris<br>carbonate, tris |

Table I-continued

| Structure | Result | Buffer |
|---|---|---|
| (quinolinium-NHNHSO₂-C₆H₄-CH₃, N-CH₃, pts⁻) | (1) neg.<br>(2) neg.<br>(3) pos.-orange — all 3<br>(4) pos.-orange-brown — all 3<br>(5) neg | |
| (piperidinium-NHNH-SO₂-C₆H₄-CH₃, N-CH₃, pts⁻) | (1) pos.-violet — all 3<br>(2) pos.-pink — carbonate, tris<br>(3) neg.<br>(4) neg.<br>(5) neg. | |

II. Dye-Providing Material Structure

| Compound | Reaction-Color | Buffer System |
|---|---|---|
| $C_{25}H_{24}N_2O_5$ | pos.-red | borate, tris |
| $C_{21}H_{14}Br_2N_2O$ | pos.-orange | borate, tris |
| $C_{24}H_{21}BrN_2O_4$ | pos.-red | carbonate, tris |
| $C_{25}H_{26}N_4O$ | pos.-aqua | all 3 |
| | neg. | |

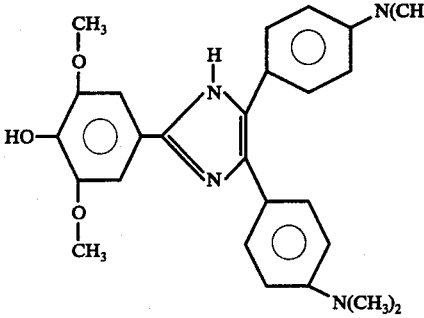

| | pos.-orange-red | all 3 |
|---|---|---|

EXAMPLE 2

An analytical element containing all the necessary reagents for the quantitative analysis of uric acid, in blood serum, was prepared in the following manner. A sample of a gelatin subbed 7 mil poly(ethylene terephthalate) film support was coated with a reagent layer comprising gelatin (10.8 g/m$^2$), peroxidase (2,000 U/m$^2$), 2-(5-bromo-4-hydroxy-3-methoxyphenyl)-4,5-bis(p-dimethylaminophenyl)imidazole (323 mg/m$^2$) and bis(vinylsulfonylmethyl)ether (72 mg/m$^2$), and carbonate buffer to pH 9.02. This reagent layer was then overcoated with a layer comprising gelatin (5.4 g/m$^2$), uricase (54 U/m$^2$), and carbonate buffer to pH 9.02. An interlayer comprising poly(n-isopropylacrylamide) (322 mg/m$^2$) was then applied to the element followed by an isotropically porous spreading layer comprising titanium dioxide (56.5 g/m$^2$) and blushed cellulose acetate (8.03 g/m$^2$).

To evaluate the coated element a series of uric acid standards varying in concentration from 2.0 to 20.0 mg/dl was prepared and the coating spotted with 10 μl drops of these solutions. After 4 minutes at 25° C a spectrophotometer with a 680nm IF (interference filter) was used to measure the reflection density, $D_R$, of the element with the following results.

| Uric Acid Solution mg/dl | $D_R$ 680 nm 4 minutes at 25° C |
|---|---|
| 0 | 0.07 |
| 2.0 | 0.28 |
| 5.0 | 0.49 |
| 10.0 | 0.63 |
| 20.0 | 0.74 |

EXAMPLE 3

An analytical element containing all the necessary reagents for the quantitative analysis of uric acid, in blood serum, was prepared in the following manner. A sample of gelatin subbed 7 mil poly(ethylene terephthalate) film support was coated with a first reagent layer comprising gelatin (10.76 g/m$^2$), peroxidase (2,152 U/m$^2$), 5,5-dimethyl-1,3-cyclohexanedione (108 mg/m$^2$), dye precursor 2-(4-hydroxy-3-methoxyphenyl)-4,5-bis(p-dimethylaminophenyl)imidazole (322 mg/m$^2$), and borate buffer at pH 8.7. The above described layer was then overcoated with a second reagent layer comprising gelatin (5.15 g/m$^2$), uricase (54 U/m$^2$), and borate buffer to maintain pH at 8.7. The element was then overcoated with an interlayer and a spreading layer as described in Example 2.

To evaluate the coated element a series of uric acid standards varying in concentration from 2 to 20 mg/dl was prepared and the coating spotted with 10 μl drops of these solutions. After 4 minutes at 30°C a spectrophotometer with a 680 IF was used to measure the reflection density, $D_R$, of the element with the following results.

| Uric Acid Solution (mg/dl) | $D_R$ 680 nm 4 minutes at 30° C |
|---|---|
| 2.0 | 0.30 |
| 10.0 | 0.82 |
| 20.0 | 1.16 |

The results of these tests demonstrate the response of the analytical element of the present invention to uric acid standards.

EXAMPLE 4

An analytical element containing all the necessary reagents for the quantitative analysis of uric acid in blood serum was prepared in the following manner. A sample of gelatin subbed 7 mil poly(ethylene terephthalate) film support was coated with a reagent layer comprising gelatin (10.8 g/m$^2$), peroxidase (6,456 U/m$^2$), a dispersion of 2-(4-hydroxy-3-methoxyphenyl-4,5-bis(p-dimethylaminophenyl)imidazole (0.54 g/m$^2$) in diethyl lauramide (5.40 g/m$^2$), and a buffer consisting of $H_3BO_3$ (0.11 g/m$^2$), KCl (0.13 g/m$^2$), and NaOH to adjust pH to 8.8. The above described reagent layer was then overcoated with a second reagent layer of gelatin (5.38 g/m$^2$), uricase (216 U/m$^2$), and a buffer consisting of $H_3BO_3$ (0.06 g/m$^2$), KCl (0.07 g/m$^2$), and NaOH to adjust pH to 9.0. An interlayer comprising poly(n-isopropyl acrylamide) (0.32 g/m$^2$) was then applied to the element. An isotropically porous spreading layer comprising titanium dioxide (46.50 g/m$^2$), blushed cellulose acetate (6.62 g/m$^2$), and Triton X-100 (3.6 g/m$^2$) was then formed upon drying an applied layer including a mixture of these components in an organic solvent.

To evaluate the coated element a series of uric acid standards varying in concentration from 5.0 to 20.0 mg/dl was prepared and the coating spotted with 10 μl drops of these solutions. After 4 minutes at 25° C a spectrophotometer with a 680 IF was used to measure the reflection density element with the following results.

| Uric Acid Solution mg/dl | $D_R$ 680 nm 4 minutes at 25° C |
|---|---|
| 5.0 | 0.69 |
| 10.0 | 1.03 |

| Uric Acid Solution mg/dl | $D_R$ 680 nm 4 minutes at 25° C |
|---|---|
| 20.0 | 1.46 |

The invention has been described in detail with particular reference to certain preferred embodiments thereof, but it will be understood that variations and modifications can be effected within the spirit and scope of the invention.

What is claimed is:

1. In a composition for the determination of hydrogen peroxide in aqueous solution, said composition comprising a substance having peroxidative activity and a dye-providing material which undergoes a detectable change upon contact with hydrogen peroxide and the substance having peroxidative activity, the improvement wherein the dye-providing material comprises:

a triarylimidazole of the formula

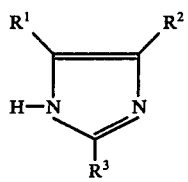

wherein $R^1$, $R^2$, and $R^3$ are each an organic group such that at least one of $R^1$, $R^2$, and $R^3$ is an ortho or para hydroxy substituted aryl group of up to 18 carbon atoms; the other two $R^1$, $R^2$, and $R^3$ being aryl groups chosen such that the oxidation potential of the imidazole lies between $-70$ mV to $+110$ mV measured by cyclic voltometry against a standard calomel electrode using a carbon based electrode.

2. The composition of claim 1 wherein the dye providing material contains a triarylimidazole of the formula

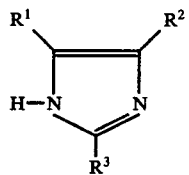

wherein $R^1$, $R^2$ and $R^3$ are each aryl or substituted aryl groups of up to 18 carbon atoms, such that at least one of $R^1$, $R^2$ and $R^3$ is an ortho or para hydroxy substituted aryl group; and at least one other of $R^1$, $R^2$ and $R^3$ has an ortho or para electron donating substituent group.

3. The composition of claim 2 wherein the ortho or para electron donating substituent group is an alkoxy group having the formula —OR wherein R is an alkyl group of 1 to about 8 carbon atoms, an aryloxy group or a dialkylamino group having the formula

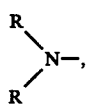

wherein R is an alkyl group of 1 to about 8 carbon atoms.

4. The composition of claim 1 wherein dyeproviding material contains a triarylimidazole selected from the group consisting of: 2-(4-hydroxy-3,5-dimethoxyphenyl)4,5-bis(4-methoxyphenyl)-imidazole; 2-(3,5-dibromo-4-hydroxyphenyl)4,5-diphenylimidazole; 2-(3-bromo-5-methoxy-4-hydroxyphenyl)-4,5-bis(4-methoxyphenyl)-imidazole; 4,5-bis (4-dimethylaminophenyl)-2-(4-hydroxyphenyl)-imidazole; 4,5-bis (4-dimethylaminophenyl)-2-(4-hydroxy-3-methoxyphenyl) imidazole; 2-(4-hydroxyphenyl)4,5-bis(4-methoxyphenyl) imidazole; and 4,5-bis(4-dimethylaminophenyl)-2-(4-hydroxy)3,5-dimethoxyphenyl)imidazole.

5. In a composition for the detection of uric acid in aqueous solution, said composition comprising uricase, buffer, substance having peroxidative activity and a dye-providing material which undergoes a detectable change upon contact with hydrogen peroxide, in the presence of the substance having peroxidative activity, said hydrogen peroxide produced by the action of uricase of uric acid, the improvement wherein the dye-providing material comprises:

a triarylimidazole of the formula

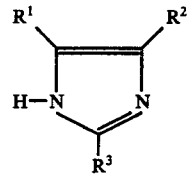

wherein $R^1$, $R^2$, and $R^3$ are each an organic group such that at least one of $R^1$, $R^2$, and $R^3$ is an ortho or para hydroxy substituted aryl group of up to 18 carbon atoms; the other two $R^1$, $R^2$, and $R^3$ being aryl groups chosen such that the oxidation potential of the imidazole lies between $-70$ mV to $+100$ mV measured by cyclic voltometry against a standard calomel electrode using a carbon based electrode.

6. The composition of claim 5 wherein the dye-providing material contains triarylimidazole of the formula

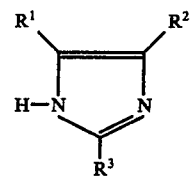

wherein $R^1$, $R^2$ and $R^3$ are each an aryl group of up to 18 carbon atoms, such that at least one of $R^1$, $R^2$ or $R^3$ is an ortho or para hydroxy substituted aryl group and at least one other of $R^1$, $R^2$ and $R^3$ has an ortho or para electron donating substituent group.

7. The composition of claim 5 wherein the ortho or para electron donating substituent group is an alkoxy group having the formula —OR wherein R is an alkyl group of from 1 to about 8 carbon atoms, an aryloxy group or a dialkylamino group having the formula:

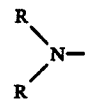

wherein R is an alkyl group of 1–8 carbon atoms.

8. The composition of claim 6 wherein the dye-providing material contains a triarylimidazole selected from the group consisting of: 2-(4-hydroxy-3,5-dimethoxyphenyl)-4,5-bis(4-methoxyphenyl)-imidazole; 2-(3,5-dibromo-4-hydroxyphenyl)4,5-diphenylimidazole; 2-(3-bromo-5-methoxy-4-hydroxyphenyl)-4,5-bis(4-methoxyphenyl)-imidazole; 4,5-bis(4-dimethylaminophenyl)-2-(4-hydroxyphenyl)-imidazole; 4,5-bis(4-dimethylaminophenyl)-2-(4-hydroxy-3-methoxyphenyl) imidazole; 2-(4-hydroxyphenyl)-4,5-bis(4-methoxyphenyl) imidazole; and 4,5-bis(4-dimethylzminophenyl)-2-(4-hydroxy)3,5-dimethoxyphenyl)imidazole.

9. A composition for the assay of aqueous liquid for a predetermined analyte comprising (a) an enzyme which effects the production of hydrogen peroxide upon contact with said analyte and (b) a hydrogen peroxide detection composition comprising
(I) a substance having peroxidative activity,
(II) a buffer,
(III) a dye-providing material which is a triarylimidazole of the formula

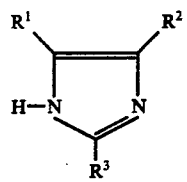

wherein $R^1$, $R^2$, and $R_3$ are each an organic group such that at least one of $R^1$, $R^2$, and $R^3$ is an ortho or para hydroxy substituted aryl group of up to 18 carbon atoms; the other two $R^1$, $R^2$, and $R^3$ being aryl groups chosen such that the oxidation potential of the imidazole lies between $-70$ mV to $+100$ mV measured by cyclic voltometry against a standard calomel electrode using a carbon based electrode.

10. The composition of claim 9 wherein the dye-providing material contains a triarylimidaxole of the formula

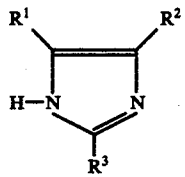

wherein $R^1$, $R^2$ and $R^3$ are each an aryl group of up to 18 carbon atoms, such that at least one of $R^1$, $R^2$ and $R^3$ is an ortho or para hydroxy substituted aryl group; and at least one other of $R^1$, $R^2$ and $R^3$ has an ortho or para electron donating substituent group.

11. The composition of claim 10 wherein the ortho or para electron donating substituent group is an alkoxy group having the formula —OR where R is an alkyl group of from 1 to about 8 carbon atoms, an aryloxy group of a dialkylamino group having the formula

wherein R is an alkyl group of 1 to about 8 carbon atoms.

12. The composition of claim 9 wherein the dye-providing material contains a triarylimidazole selected from the group consisting of: 2-(4-hydroxy-3,5-dimethoxyphenyl)-4,5-bis(4-methoxyphenyl)-imidazole; 2-(3,5-dibromo-4-hydroxyphenyl)4,5-diphenylimidazole; 2-(3-bromo-5-methoxy-4-hydroxyphenyl)-4,5-bis(4-methoxyphenyl)-imidazole; 4,5-bis(4-dimethylaminophenyl)-2-(4-hydroxyphenyl)-imidazole; 4,5-bis(4-dimethylaminophenyl)-2-(4-hydroxy-3-methoxyphenyl) imidazole; 2-(4-hydroxyphenyl)4,5-bis(4-methoxyphenyl) imidazole; and 4,5-bis(4-dimethylaminophenyl)-2-(4-hydroxy)3,5-dimethoxyphenyl)imidazole.

13. In a method for assaying an aqueous liquid for hydrogen peroxide content comprising contacting a sample of the aqueous liquid with a buffered composition comprising a substance having peroxidative activity and a dye-providing material which is oxidized in the presence of hydrogen peroxide and said substance having peroxidative activity to provide a dye, the improvement comprising using as the dye-providing material

a triarylimidazole of the formula

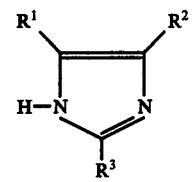

wherein $R^1$, $R^2$, $R^3$ are each an organic group such that at least one of $R^1$, $R^2$, and $R^3$ is an ortho or para hydroxy substituted aryl group of up to 18 carbon atoms; the other two $R^1$, $R^2$, and $R^3$ are aryl groups chosen such that the oxidation potential of the imidazole lies between $-70$ mV to $+110$ mV measured by cyclic voltometry against a standard calomel electrode using a carbon based electrode.

14. The method of claim 13 wherein the dye-providing material contains a triarylimidazole of the formula

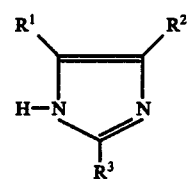

wherein $R^1$, $R^2$ and $R^3$ are each aryl or substituted aryl groups of up to 18 carbon atoms, such that at least one of $R^1$, $R^2$ and $R^3$ is an ortho or para hydroxy substituted aryl group; and at least one other of $R^1$, $R^2$ and $R^3$ has an ortho or para electron donating substituent group.

15. The method of claim 14 wherein the ortho or para electron donating substituent group is an alkoxy group having the formula —OR where R is an alkyl group of from 1 to about 8 carbon atoms, an aryloxy group or a dialkylamino group

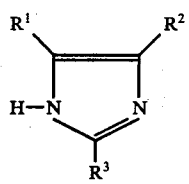

wherein R is an alkyl group of from 1 to about 8 carbon atoms.

16. The composition of claim 14 wherein dye-providing material contains a triarylimidazole selected from the group consisting of: 2-(4-hydroxy-3,5-dimethoxyphenyl)-4,5-bis(4-methoxyphenyl)-imidazole; 2-(3,5-dibromo-4-hydroxyphenyl)4,5-diphenylimidazole; 2-(3-bromo-5-methoxy-4-hydroxyphenyl)-4,5-bis(4-methoxyphenyl)-imidazole; 4,5-bis(4-dimethylaminophenyl)-2-(4-hydroxphenyl)-imidazole; 4,5-bis(4-dimethylaminophenyl)-2-(4-hydroxy-3-methoxyphenyl) imidazole; 2-(4-hydroxyphenyl)4,5-bis(4-methoxyphenyl) imidazole; and 4,5-bis(4dimethylaminphenyl)-2-(4-hydroxy)3,5-dimethoxyphenyl)imidazole.

17. An element for the detection of uric acid in aqueous liquid, the element comprising a non-fibrous, isotropically porous spreading layer and a reagent layer and containing (a) uricase and (b) a hydrogen peroxide detection composition comprising
(I) a substance having peroxidative activity,
(II) a buffer,
(III) and a dye-providing material which is a triarylimidazole of the formula t,680
wherein $R^1$, $R^2$, and $R^3$ are each an organic group such that at least one of $R^1$, $R^2$, and $R^3$ is an ortho or para hydroxy substituted aryl group of up to 18 carbon atoms; the other two $R^1$, $R^2$, and $R^3$ being aryl groups chosen such that the oxidation potential of the imidazole lies between $-70$ mV to $+110$ mV measured by cyclic voltometry against a standard calomel electrode using a carbon based electrode.

18. The element of claim 17 wherein the dye-providing material contains a triarylamidazole of the formula

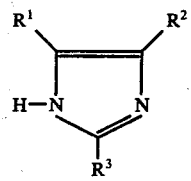

wherein $R^1$, $R^2$ and $R^3$ are each aryl groups of up to 18 carbon atoms, such that at least one of $R^1$, $R^2$ and $R^3$ is an ortho or para hydroxy substituted aryl group; and at least one other of $R^1$, $R^2$ and $R^3$ has an ortho or para electron donating substituent group.

19. The element of claim 18 wherein the ortho or para electron donating substituent group is an alkoxy group —OR where R is an alkyl group of 1 to about 8 carbon atoms, an aryloxy group or a dialkylamino group

wherein R is an alkyl group of 1 to about 8 carbon atoms.

20. The element of claim 18 wherein the dye-providing material contains a triarylimidazole selected from the group consisting of: 2-(4-hydroxy-3,5-dimethoxyphenyl)4,5-bis(4-methoxyphenyl)-imidazole; 2-(3,5-dibromo-4-hydroxyphenyl)4,5-diphenylimidazole; 2-(3-bromo-5-methoxy-4-hydroxyphenyl)-4,5-bis(4-methoxyphenyl)-imidazole; 4,5-bis(4-dimethylaminophenyl)-2-(4-hydroxphenyl)-imidazole; 4,5-bis(4-dimethylaminophenyl)-2-(4-hydroxy-3-methoxyphenyl) imidazole; 2-(4-hydroxyphenyl)4,5-bis(4-methoxyphenyl) imidazole; and 4,5-bis(4-dimethylaminophenyl)-2-(4-hydroxy)3,5-dimethoxyphenyl)imidazole.

* * * * *